United States Patent [19]
Brocard et al.

[11] Patent Number: 6,127,543
[45] Date of Patent: Oct. 3, 2000

[54] ANTIMALARIAL ORGANOMETALLIC IRON COMPLEXES

[75] Inventors: Jacques Brocard, Faches Thumesnil, France; Jacques Lebibi, Franceville, Gabon; Lucien Maciejewski, Villeneuve d'Ascq, France

[73] Assignee: Université des Sciences et Technologies de Lille, Villeneuve d'Ascq, France

[21] Appl. No.: 08/952,093

[22] PCT Filed: May 10, 1996

[86] PCT No.: PCT/FR96/00721

§ 371 Date: Jan. 29, 1998

§ 102(e) Date: Jan. 29, 1998

[87] PCT Pub. No.: WO96/35698

PCT Pub. Date: Nov. 14, 1996

[30] Foreign Application Priority Data

May 10, 1995 [FR] France .................................. 95 05532

[51] Int. Cl.$^7$ ...................... A61K 31/47; A61K 31/4706; A61K 31/5377; C07D 453/04
[52] U.S. Cl. ...................... 546/176; 514/311; 514/235.2; 514/252; 540/128; 540/363; 546/159; 546/160
[58] Field of Search .................................. 546/176, 159, 546/160; 540/128, 363; 514/34, 253.2, 252

[56] References Cited

FOREIGN PATENT DOCUMENTS

| | | |
|---|---|---|
| 0 004 894 | 10/1979 | European Pat. Off. . |
| 0 214 933 A2 | 3/1987 | European Pat. Off. . |
| 1 470 210 | 4/1997 | United Kingdom . |

OTHER PUBLICATIONS

Geary, Timothy G. et al., "Effects Of Antibiotics On Plasmodium Falciparum In Vitro," *Am J. Trop. Med. Hyg.*, vol. 32, No. 2, pp. 221–225 (1983).

Barclay, A.J.G. et al., "Tick–borne relapsing fever in central Tanzania,"*Transactions of the Royal Society of Tropical Medicine and Hygiene*, vol. 84, pp. 852–856 (1990).

van Zyl, Robyn et al., "The combined effect of iron chelators and classical animalarials on the in–vitro growth of *Plasmodium falciparum*," *Journal of Antimicrobial Chemotherapy*, vol. 30, pp. 273–278 (1992).

MEDLINE 91263174, abstract of Barclay, Transactions of the Royal Society of Tropical Medicine and Hygiene, vol. 84(6), pp. 852–856, Nov.–Dec. 1990.

MEDLINE 83176127, abstract of Geary, American J of Tropical Med and Hygiene, Mar. 1983, vol. 32(2), pp. 221–225.

Chemical Abstracts 106:169037, abstract of EP 214933, Jung, 1987.

Chemical Abstracts 117:248458, abstract of Van Zyl, J Antimicrob Chemother, 1992, vol. 30(3), pp. 273–278.

Ong, Chi Wi, et al.; "A ferrocene–intercalator conjugate with a potent cytotoxicity"; Chemical Abstracts; Sep. 27, 1993; vol. 119(13):33; Abstract No.: 131035p.

Klimova, Ye, I., et al.; "Biological activity of ferrocenyl–substituted derivatives of $\Delta^4$–tetrahydrophthalic acid"; Chemical Abstracts; Jan. 16, 1995; vol. 122(3):959; Abstract No.: 31669s.

Chemical Abstracts 109:276, abstract of Constantinidis, J Am Chem Soc, vol 110(13), pp.4391–4395, 1988.

Chemical Abstracts 119:216188, abstract of Singh, Asian J Chem, 5(2), pp.348–351, 1993.

Chemical Abstracts 109:203784, abstract of Wasi, Synth Rect Inorg Met–Org Chem, 18(5), pp.473–485.

Chemical abstracts 112:11926, Edwards, GB 2208599, 1989.

Chemical Abstracts 119:63053, Libman, WO 9300082, 1993.

Chemical Abstracts 97:120204, Scovill, J Med Chem, 25(10), pp.1261–1264, 1982.

Chemical Abstracts 92:94213, Nickel, Arch Pharm (Weinheim, Ger), 312(11), pp.97197–2, 1979.

*Primary Examiner*—D. Margaret Seaman
*Attorney, Agent, or Firm*—Venable; Michael A. Gollin; Keith G. Haddaway

[57] ABSTRACT

Organometallic iron complexes containing one or more basic structural components characterizing a molecule with antimalarial properties such as quinine, chloroquinine or mepacrine, as well as one or more iron atoms are described. The complexes of the invention are more particularly characterized in that they contain one or more ferrocene groups.

17 Claims, No Drawings

ANTIMALARIAL ORGANOMETALLIC IRON COMPLEXES

The invention relates to organometallic iron complexes exhibiting particularly advantageous properties as antimalarial agents. The invention relates in particular to the insertion of ferrocenyl groups into the structure of molecules possessing antimalarial properties.

For many years, malaria has continued to be a major cause of death in many developing countries. The erosion of the chemotherapeutical weaponry linked to the development of resistance in the strains is one of the principal problems encountered in the fight against malaria. Chloroquinine is the most widely used antimalarial worldwide and chloroquinine-resistant strains have appeared in all malaria zones. It is therefore possible that ultimately, the difficulties encountered in the treatment of malaria-related infections will be increasingly important. Although considerable resources are dedicated to the fight against malaria, few alternatives to the medicaments currently used have been proposed.

The inventors have discovered that by combining with molecules having a structure close to that of antimalarials one or more iron atoms, for example by means of the insertion of a ferrocenyl group inside analogs of substances such as quinine, chloroquinine, mepacrine and primaquine, the therapeutic activity of these substances was substantially increased. The inventors have also discovered that the use of the compounds of the invention makes it possible to avoid the relapses in the long term which are often associated with conventional antimalarial treatments.

The high rate of reproduction of *Plasmodium falciparum* and its iron use have led to attempts at destruction by the privation of iron in the use of ferrioxamine hydroxyamates. Although these tests have given satisfactory results, the inventors have oriented their strategy towards a reverse approach. It involves using instead the affinity of plasmodium for iron to increase the probability of encountering the antimalarial molecule.

The use of organometallic complexes so far remains marginal in therapeutic chemistry. Ferrocene in particular appears only in analogs of prostaglandins, Ferroceron (a drug used to combat iron deficiencies), and analogs of hexestrol.

The invention therefore relates to organometallic iron complexes comprising at least one of the structural components characteristic of a molecule possessing antimalarial properties as well as one or more iron atoms. The reference to structural components characteristic of a molecule possessing antimalarial properties is used to designate certain characteristic portions of antimalarial molecules which confer on these molecules their properties.

Structural components characteristic of molecules possessing antimalarial properties are varied and can be easily recognized by persons skilled in the art. The need to use the basic structure determining the antimalarial activity should be noted, however. For example, in the case of the quinines, the presence of an amino alcohol substituent on the quinoline is essential, just as a diamine substituent on the quinoline is essential for the modified molecules of the chloroquinine type, just as a substituent is essential for the modified molecules of the mepacrine type. For these molecules, the quinolines or the acridines are considered as basic structural components conferring the desired antimalarial properties.

It was therefore a question of reproducing as accurately as possible the basic structure of these molecules while attaching thereto, and preferably while inserting therein, substituents which make it possible to confer an organometallic character on these molecules. The invention is therefore based on the combination of an iron atom and an organic ligand close to molecules whose antimalarial properties are known. Preferably, the iron is provided by ferrocene whose chemistry is known and of which several derivatives are commercially available.

It is important to underline here that the inventors have not sought solely to graft a molecule containing iron atoms (ferrocene for example) onto existing antimalarial compounds. Organic synthesis constraints would have made this type of operation difficult, but in any case, the inventors were seeking instead to position the iron atoms so as to make them as easily accessible as possible to the desired *Plasmodium falciparum* strains.

In fact, the inventors have sought to replace a hydrophobic part with a ferrocenyl group for example, and to place this ferrocenyl group inside the molecule so as to cause the least possible disruption in the overall geometry of the assembly. The choice of the position of the ferrocenyl is therefore dependent on a place on the molecule where the geometric alterations cause the least possible modifications in the overall structural effects of the molecule.

According to one of the preferred embodiments, the organometallic iron complexes of the invention comprise at least one of the following basic structural components:

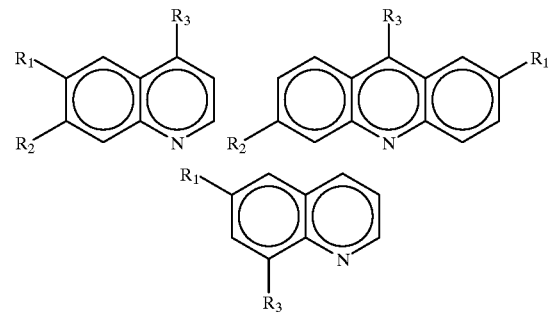

in which R1 is hydrogen, alkyl, alkoxy, acyl, halogen or etheralkyl aldehyde, hydroxyl, hydroxyalkyl, alkoxyalkyl, acyloxyalkyl, acetylalkyl, preferably hydrogen or ethermethyl;

R2 is hydrogen, alkyl, alkoxy, halogen, acyl or etheralkyl aldehyde, hydroxyl, hydroxyalkyl, alkoxyalkyl, acyloxyalkyl, acetylalkyl, preferably hydrogen or halogen; and R3 is an amine or hydroxyalkyl group which can be linked to a ferrocenyl group by means of a covalent bond;

as well as the salts of these compounds, for example the tartrate or ditartrate salts.

Preferably, when the term alkyl is used in the context of the present invention, it refers to an alkyl having between 1 and 10, preferably between 1 and 4 carbon atoms.

Although ferrocene appears to be the substituent of choice for conferring an organometallic character on the compounds of the invention, it is possible to envisage the use of other substituents which would allow the presentation of one or more iron atoms capable of being absorbed by the infecting plasmodium strain. It is therefore possible to envisage, inter alia, the use of substituents such as the iron-tricarbonyl diene.

According to another preferred embodiment of the invention, the organometallic iron complex is characterized in that it possesses the following structure:

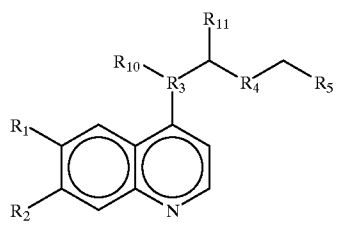

in which
R1, R2 and R3 are as defined above;
R4 is an alkyl, alkoxy, acyl, hydroxyalkyl, acyloxyalkyl, acetylalkyl or ferrocenyl group;
R5 is an amine group, substituted or otherwise, preferably with one or more alkyl, particularly methyl, groups or with one or more ferrocenyl groups;
R10 is hydrogen, alkyl or an alkyl-ferrocenyl group; and
R11 is hydrogen or alkyl.

Among the particularly advantageous compounds, the use of the compounds having the following structure is envisaged:

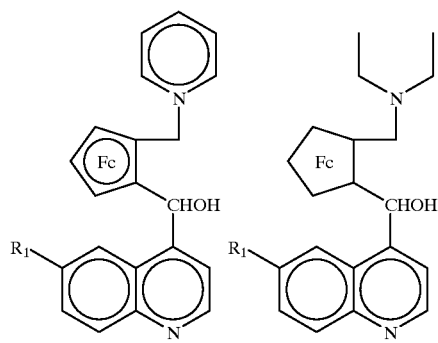

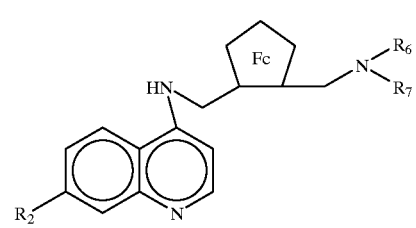

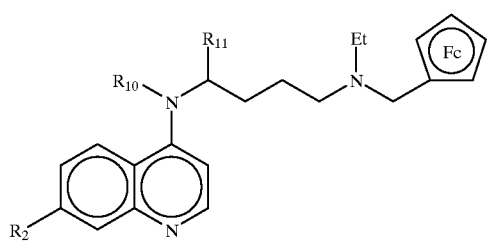

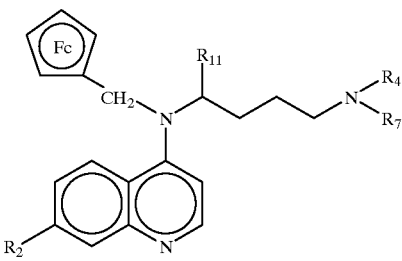

in which
R1, R2, R4, R10 and R11 are as defined above; and
R6 and R7 are identical or different and are selected from hydrogen, alkyl-ferrocenyl, ferrocenyl, alkyl, particularly methyl or ethyl, but also the group

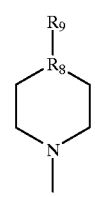

where R8 is a —CH— or a heteroatom, and R9 is hydrogen, alkyl, alkoxy, acyl, halogen or etheralkyl aldehyde, hydroxyl, hydroxyalkyl, alkoxyalkyl, acyloxyalkyl, acetylalkyl, to form, preferably, the groups piperidino

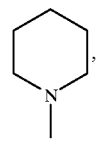

morpholino

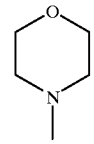

or piperazino

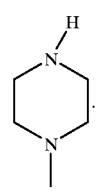

The group

represents a ferrocene substituent as known by persons skilled in the art.

The invention also relates to the compounds comprising an acridine group and possessing the following structure:

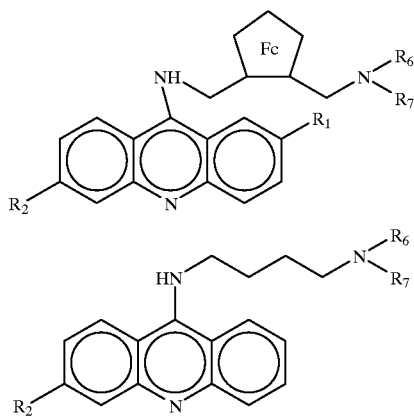

in which R1, R2, R6 and R7 are as defined above.

Furthermore, the invention relates to organometallic complexes which can be considered as analogs of primaquine having the following structure:

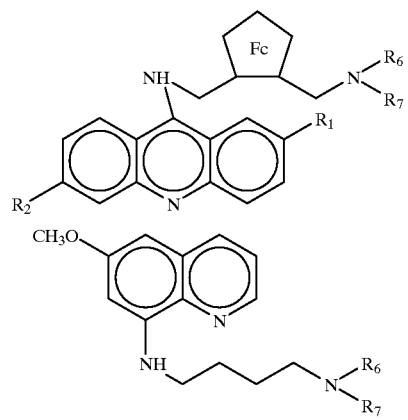

in which R6 and R7 are as defined above.

The invention also relates to pharmaceutical compositions comprising one of the compounds described above in combination with an acceptable pharmaceutical excipient as well as a method for the treatment of malaria which consists in administering to a patient a therapeutic dose of one of the compounds mentioned above.

Tests in vitro and in vivo carried out to determine the activity of the organometallic complexes of the invention on laboratory strains and field strains have been carried out. The in vitro tests, which are based on the assimilation of radioactive hypoxanthine by parasites, have demonstrated that the organometallic complexes of the invention have, in general, a greater action on the inhibition of parasitemia that the compounds normally used such as chloroquinine and quinine. Furthermore, tests have demonstrated a marked action on a chloroquinine-resistant strain.

PREPERATION OF SOME PREFERRED EMBODIMENTS OF THE ORGANOMETALLIC IRON COMPLEXES OF THE INVENTION

The synthesis of the organometallic complexes of the invention involves conventional methods of organometallic chemistry, that is to say the Mannich reaction, lithiation and condensation with an aldehyde. For example, the passage of ferrocene to dialkylaminomethylferrocene by the reaction of methanal and dialkylamine (or piperidine or di(dialkylamino)methane is known. It is the Mannich reaction. The choice of amine makes it possible to vary the alkyl chains carried by the nitrogen in the final product. Lithiation is also described in the literature. Condensation with 4-formylquinoline leads to the desired compound. Following this method and based on certain model molecules, the following molecules are synthesized:

1) Model Molecule=Quinine Synthesis 1

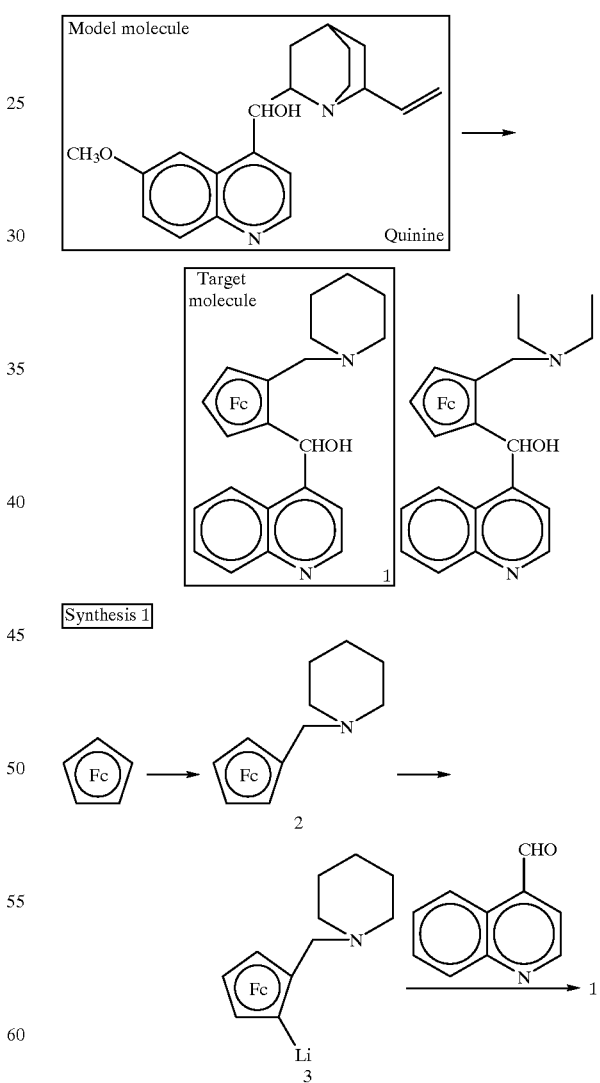

The passage of ferrocene to dialkylaminomethyl ferrocene 2 by the action of methanal and a dialkylamine (or piperidine) or of di(dialkylamino)methane is known (MANNICH reaction). The choice of amine makes it possible to vary the alkyl chains carried by the nitrogen in the final product. The lithiation of 2 is described in the literature. The condensation of 3 with 4-formylquinoline will lead to 1. Stereochemical study of this product, which carries two chiral centers, will be carried out.

2) Model Molecule=Chloroquinine Syntheses 2 and 3

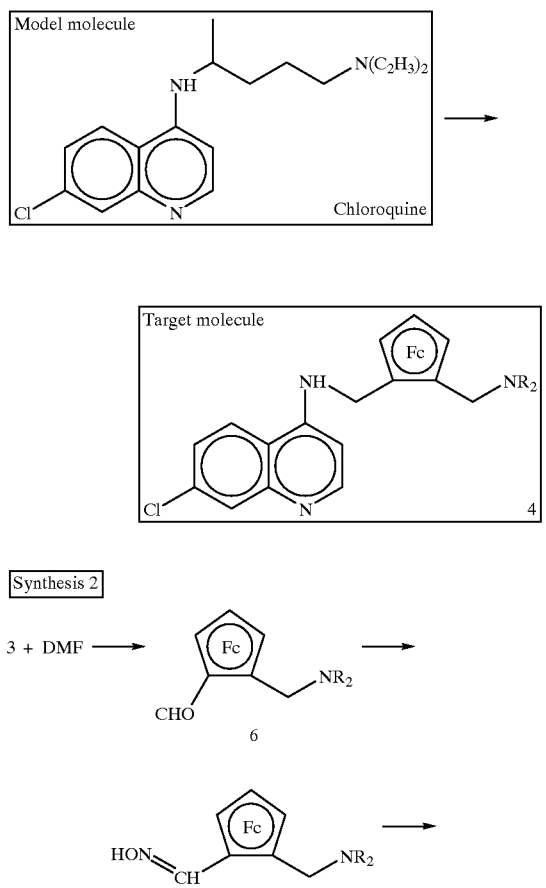

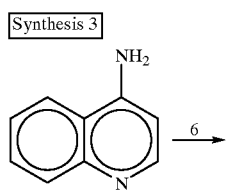

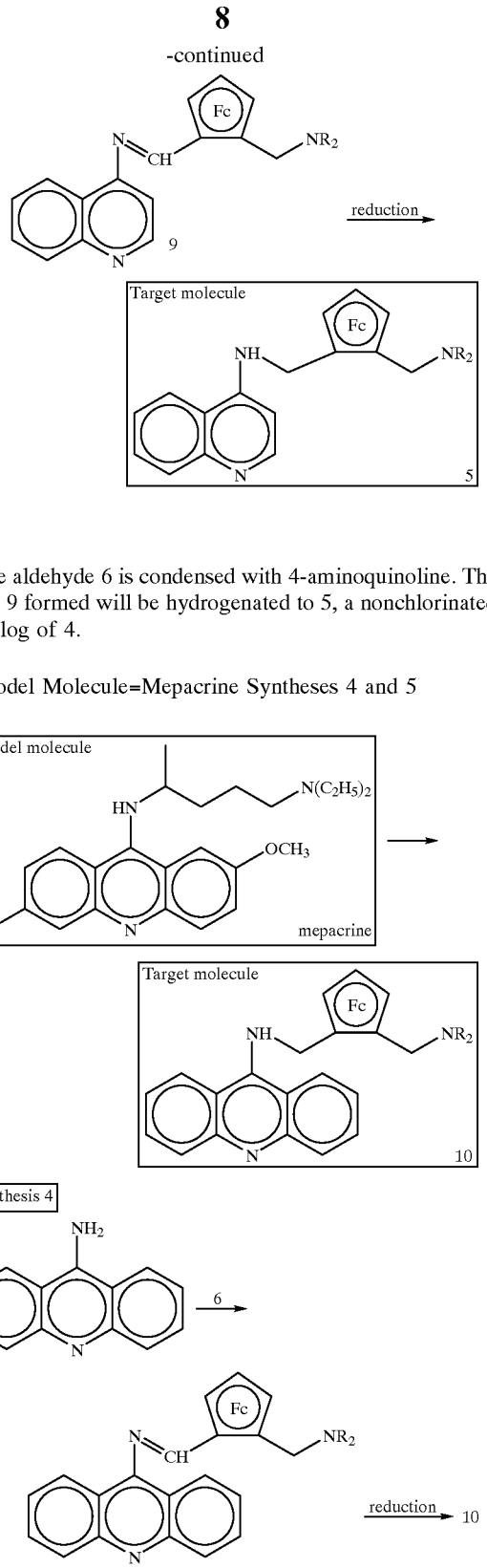

The aldehyde 6 is condensed with 4-aminoquinoline. The imine 9 formed will be hydrogenated to 5, a nonchlorinated homolog of 4.

3) Model Molecule=Mepacrine Syntheses 4 and 5

The condensation of 3 with dimethylformamide leads to the aldehyde 6. The oximation and the reduction of 6 give 7 and then 8. The condensation of 8 with 4-7-dichloroquinoline leads to compound 4.

The aldehyde D is condensed with 6-aminoacridine, which is commercially available. The imine formed will be halogenated to 10, a nonchlorinated and nonmethoxylated homolog of mepacrine.

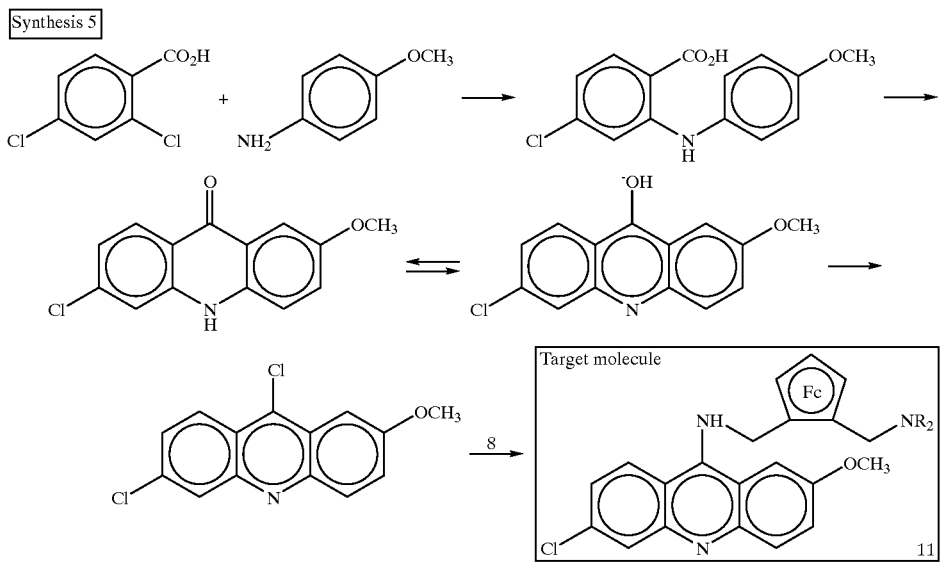

This synthesis, known up to the dichlorinated compound, allows the introduction of the substituents present on the target molecule.

4) Model Molecule=Primaquine Syntheses 6, 7, 8 and 9

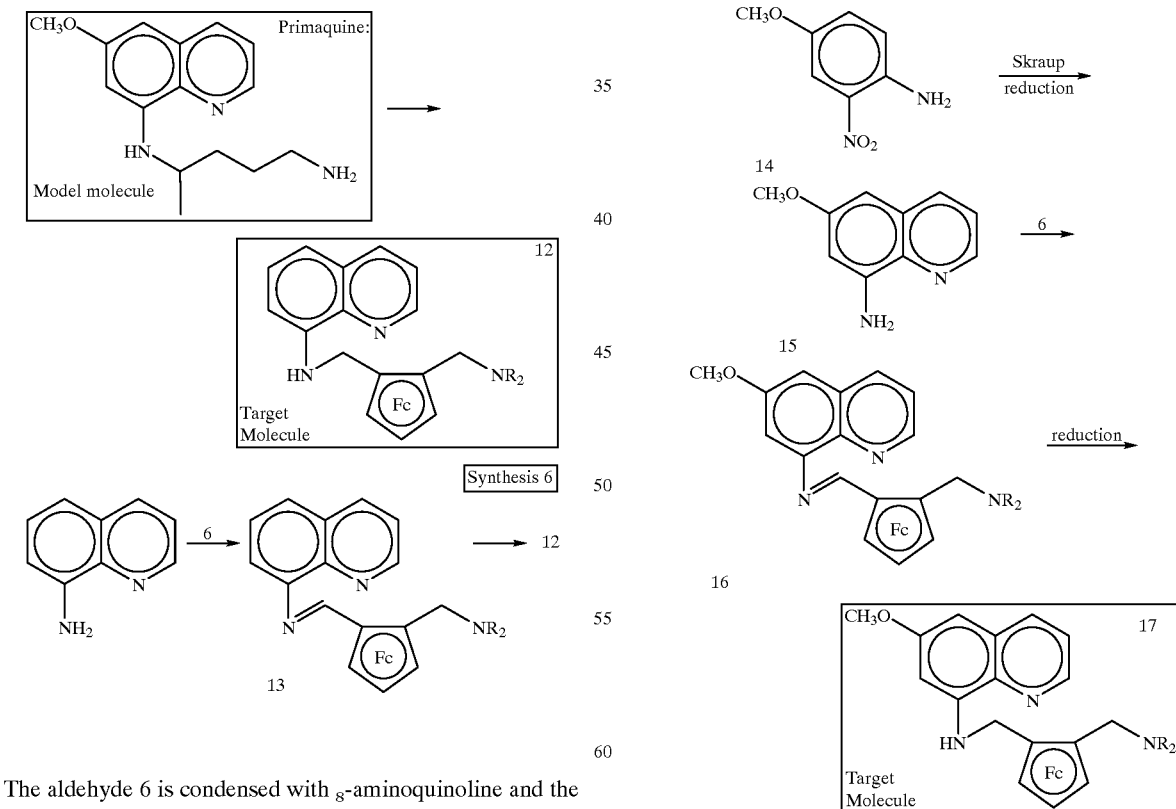

The aldehyde 6 is condensed with 8-aminoquinoline and the imine 13 is hydrogenated to 12.

The homolog of 12, methocylated at the 6-position, is obtained from 6-methoxy-8-aminoquinoline a whose preparation is known (Skraup synthesis):

The homolog methylated at the α position relative to the α secondary nitrogen is obtained by the action of 3 on acetonitrile:

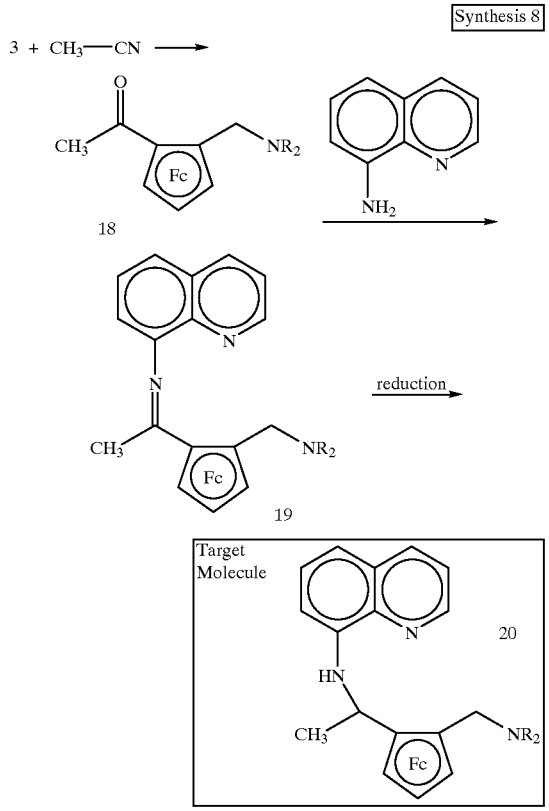
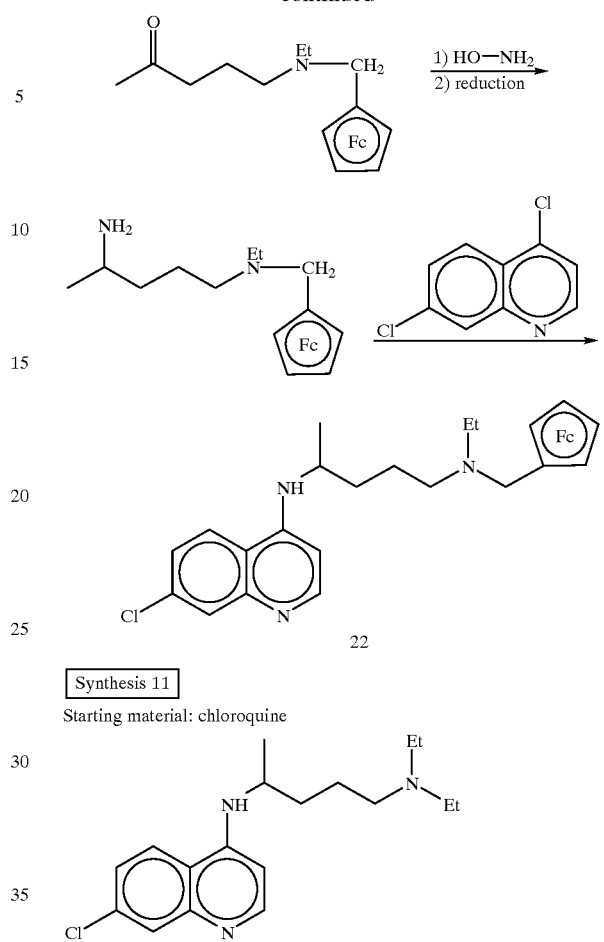
The homolog methylated at the α position relative to the secondary nitrogen and methoxylated at the 6 position, as is Primaquine, is obtained by the action of 18 on 15:
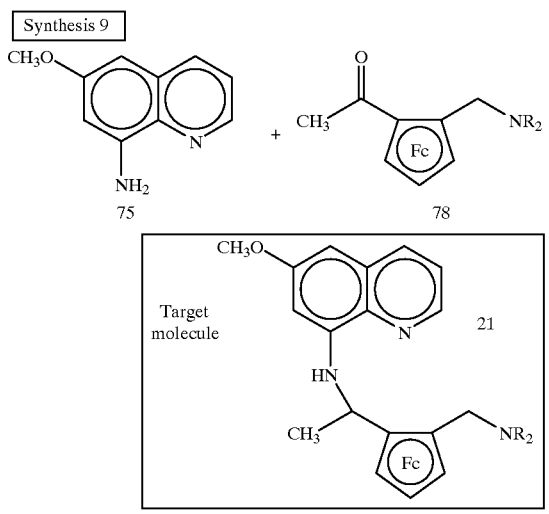
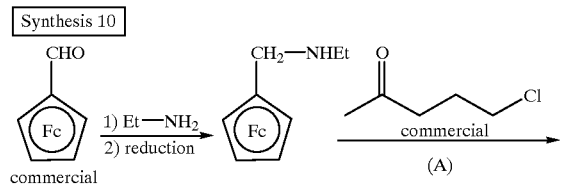
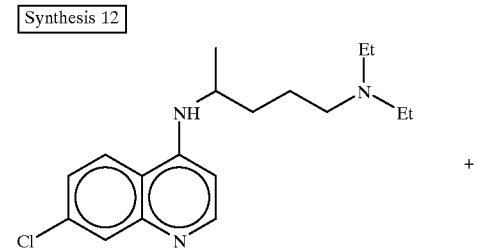

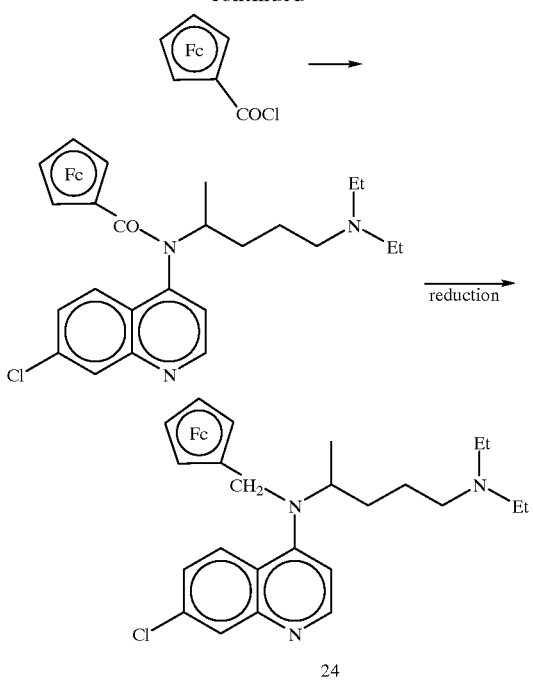

strains. The test compounds are the compounds SN1, which correspond to compound 4 in which —NR$_2$ is —N(CH$_3$)$_2$, SN$_2$ which corresponds to compound 4 in which —NR$_2$ is piperidine and OD3, which corresponds to compound 11 in which —NR'$_2$ is piperidine.

The proliferation of the parasites is measured by incorporation of $^3$[H] hypoxanthine applied to the cultures 16 hours before the end of the culture. The radioactive hypoxanthine is absorbed by the developing parasites. The quantity absorbed is measured by a Beta counter in counts per minute. The analysis is generally carried out by comparison of the IC50 values (concentration inhibiting 50% of the proliferation) calculated by linear interpolation.

The results presented in Table 1 below demonstrate that the analog SN1 of chloroquinine has, in general, a greater action on the inhibition of parasitemia than quinine and a marked action on the sole chloroquinine-resistant strain tested so far.

It has also made it possible to observe the high chloroquinine-resistance of these Francevilloises strains (IC50 between 190 and <1000 nm for the 7 strains tested).

TABLE 1

| | ID 50 (CHLOROQUININE & COMPOUND SN1) | | | | | | | |
|---|---|---|---|---|---|---|---|---|
| | Strains | | | | | | | Chloroquinine-resistant strains |
| Strain No. | 917 | 17 | 309 | 935 | 926 | 823 | 265 | 859 |
| Chloroquinine (μM) | 1.9 | 2 | 9.8 | >10 | >10 | >10 | >10 | Not determined |
| Compound D (μM) | 0.13 | 0.23 | 1.15 | 1.2 | 2.3 | 1.2 | 1.7 | 18 |
| Chloroquinine IC50 | 190 | 200 | 980 | >1000 | >1000 | >1000 | >1000 | |
| SN1 IC50 | 10 | 20 | 110 | 120 | 230 | 120 | 170 | |

These 12 syntheses lead to 12 series of molecules obtained using, for the starting MANNICH reaction, variously substituted amines. The salts of these compounds (for example the tartrate or ditartrate salts) can be easily obtained by persons skilled in the art.

REFERENCES

1) K. DOMBROWSKI, W. BALDWIN and J. SHEATS, J. Organomet. Chem., 1986, 281.
2) A. RYABOV, Angew. Chem. Int. Ed. Engl., 1991, 931.
3) G. JAOUEN and A. VESSIERES, Pure Appli. Chem. 1989, 61, 56; G. JAOUEN, A. VESSIERES, and I. Butler, Acc. Chem. Res. 1993, 26, 361; id. Organomet., 1993, 12, 4545.
4) M. GRUSELLE, B. MALESIEUX, L. TROITSKAYA, V. SOKOLOV, L. EPSTEIN, Y. SHUBRINA, Organomet., 1994, 13, 200.
5) V. SOKOLOV, L. TROISKAYA, N. KRUSKCHOVA, Izv. Acad, Nauk. SSSR, Ser. Kim., 1987, 10, 2387.
6) KOPF et al., Angew. Chem., 1984, 96, 446, id. Chem. Hev., 1987, 87, 1137.

Tests in Vitro of Organometallic Complexes of the Invention a) Field Strains

As mentioned above, the in vitro activity of organometallic complexes of the invention was measured on field b) Chloroquinine-Resistant Strains Three *P. faciparum* lines M25, chloroquinine-sensitive, and FCM 6 and FCM 17, chloroquinine-resistant, were cultured at a parasitemia rate approaching 1%, at the trophozoite stage, for a period of 48 hours. The cultures were treated with the antimalarials (chloroquinine and ferrocene analogs SN1, SN2 and OB3) at the concentrations of 10$^{-3}$, 10$^{-2}$, 10$^{-1}$, 1 and 10 μg/ml compared with a control (solvent for the antimalarials) and on untreated cultures.

The results obtained with the lines reveal an inhibition by the ferrocenyl compounds of the resistance of the strains FCM 6 and FCM 7 to chloroquinine, which is variable depending on the terminal functions attached to the ferrocene group (Table 2). The analogs remain effective on the chloroquinine-sensitive line M25. A difference in sensitivity for the compound SN2 between the lines FCM 6 and FCM 17 should be noted (which would suggest a difference in the metabolism of the molecule between these two strains).

Table 3: IC50 (in μg/ml) of chloroquinine (chloro.) and the ferrocenyl analogs (SN1, SN2, SN3) on chloroquinine-sensitive (M 25) and chloroquinine-resistant (FCM 6 and FCM 17) established lines of *P. falciparum*. Results of two experiments.

|  | chloro | SN1 | SN2 | OD3 |
|---|---|---|---|---|
| FCM17 | 0.555 | 0.057 | 0.478 | 0.058 |
| FCM17 | 0.550 | 0.055 | 0.392 | 0.058 |
| FCM6 | 0.492 | 0.054 | 0.073 | 0.528 |
| FCM6 | 0.442 | 0.052 | 0.071 | 0.056 |
| M25 | 0.069 | 0.056 | 0.055 | 0.089 |
| M25 | 0.063 | 0.049 | 0.326 | 0.083 |

The introduction of a ferrocenyl group into the molecule therefore preserves the efficacy of the chloroquinine in the chloroquinine-resistant strains. The inventors believe that the affinity of hemoglobin for iron promotes the absorption, or limits the release of chloroquinine which is particularly high in the chloroquinine-resistant strains. Moreover, the avidity of the plasmodia toward circulating iron may also explain the yield of the ferrocene compounds, especially if the parasite is incapable of metabolizing ferrocene.

Test of the in Vivo Activity of an Organometallic Iron Complex of the Invention Having a Structure Analogous to Chloroquinine From the results obtained in the context of in vitro studies, the inventors selected the compound SN1 in order to carry out in vivo studies. In order to facilitate the assimilation of the product by the body in absorption per os, a salt of this compound, SN1 ditartrate, was also tested in vitro on chloroquinine-resistant strains: the results obtained indicate a better activity of the SN1 ditartrate compound (SN1-tar) than that of the product SN1.

Methodology: the laboratory mice can be infected with various strains of rodent Plasmodium. Female SWISS mice (about 30 g) (5 per group) were inoculated on D0 with 107 $P.$ $berghei$ parasites, chloroquinine-sensitive, lethal strain. The mice were treated between D0 and D2 using 4 subcutaneous injections of chloroquinine or of compound SN1, with a total dose of 1 or 10 mg/kg of weight. The parasitemia and mortality were monitored from D3, for at least 40 days.

The compound SN1 and its salt, SN1 ditartrate, were tested.

Results:

Test of the compound SN1 and SN3-tar on $P.$ $berghei$, N strain: the result of two experiments is given in the following table:

| Groups | Dose | Mortality | |
|---|---|---|---|
|  |  | Exp 1 | Exp 2 |
| Control | 0 | 5/5 | 5/5 |
| Chloroquinine | 10 | 5/5 | 5/5 |
| Chloroquinine | 1 | 5/5 | 5/5 |
| SN1 | 10 | 1/5 | 0/5 |
| SN1 | 1 | 5/5 | 5/5 |
| SN1-tar | 10 | 0/5 | 0/5 |
| SN1-tar | 1 | 5/5 | 5/5 |

The compounds SN1 and SN1-ditartrate therefore have a better activity than chloroquinine in vivo on the strains used.

Moreover, experiments using a chloroquinine-resistant rodent Plasmodium, $P.$ $yoelii$, strain NS, and SN1 ditartrate were also carried out: no parasite could be detected in the mice treated with 10 mg/kg of SN1 ditartrate, whereas all the mice treated with the same dose of chloroquinine exhibit a high parasitemia.

The compound SN1 ditartrate is therefore active in vivo on a $P.$ $yoelii$ strain exhibiting the same type of chloroquinine-resistant as $P.$ $faciparum$. The results also demonstrate a marked decrease in the number of relapses when the compounds of the invention are used.

The inventors have also tested in vivo with $P.$ $yoelii$ the compound 23 in ditartrate salt form. The preliminary results obtained show that this compound possesses an equivalent activity to the activity of SN1-tar (tartrate salt of SN1).

We claim:

1. An organometallic iron complex having antimalarial properties and comprising at least one of the basic structural components characteristic of a molecule possessing antimalarial properties, and further comprising one or more ferrocene groups.

2. The organometallic iron complex of claim 1, which complex is a salt.

3. The organometallic iron complex of claim 2, wherein the salt is a tartrate salt or a ditartrate salt.

4. The organometallic iron complex of claim 1, wherein said structural component is selected from the following structures:

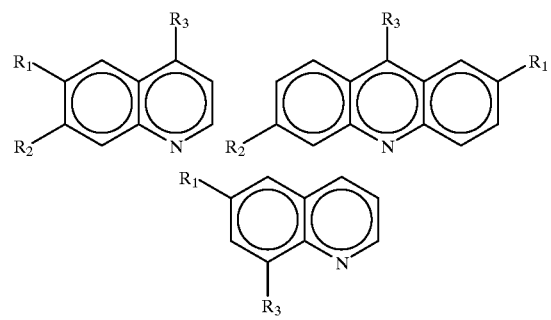

and wherein $R_1$ is hydrogen, alkyl, alkoxy, acyl, halogen or etheralkyl aldehyde, hydroxyl, hydroxyalkyl, alkoxyalkyl, acyloxyalkyl, or acetylalkyl;

$R_2$ is hydrogen, alkyl, alkoxy, halogen, acyl or etheralkyl aldehyde, hydroxyl, hydroxyalkyl, alkoxyalkyl, acyloxyalkyl, or acetylalkyl; and $R_3$ is an amine or hydroxyalkyl group which reacts with, and forms a covalent bond to, a ferrocenyl group.

5. The complex of claim 4, wherein in $R_1$ is hydrogen or etheralkyl, and/or wherein $R_2$ is hydrogen or halogen.

6. The organometallic iron complex of claim 4, which complex comprises one of the following structures:

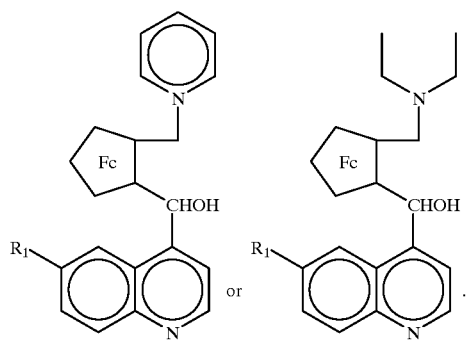

7. The organometallic iron complex of claim 1 having the following structure:

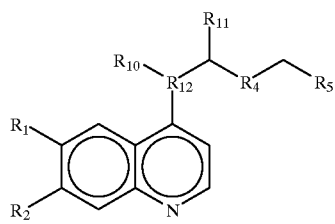

wherein $R_4$ is an alkyl, alkoxy, acyl, hydroxyalkyl, acyloxyalkyl, acetylalkyl, or ferrocene group;

$R_5$ is a substituted or unsubstituted amine group;

$R_{10}$ is a hydrogen, alkyl, or alkyl-ferrocenyl group; and $R_{11}$ is hydrogen or alkyl, and $R_{12}$ is an amine or hydroxyalkyl group which reacts with, and forms a covalent bond to, a ferrocenyl group.

8. The organometallic iron complex of claim 7, wherein $R_5$ is an amine group substituted with one or more alkyl groups or with one or more ferrocene groups.

9. The organometallic iron complex of claim 7 having one of the following structures:

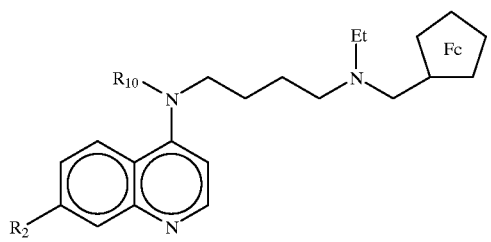

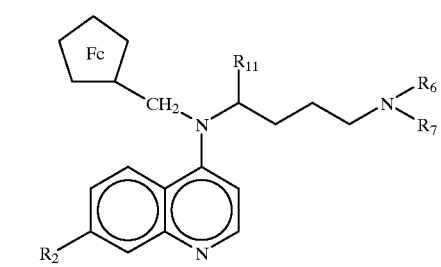

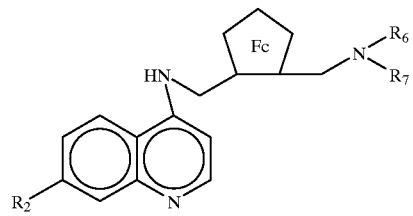

wherein $R_6$ and $R_7$ are independently selected from the group consisting of hydrogen, alkyl-ferrocene, ferrocene, and alkyl, and the group

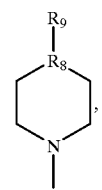

where $R_8$ is —CH$_2$— or a heteroatom, and $R_9$ is hydrogen, alkyl, acyl, halogen or etheralkyl aldehyde, hydroxyl, hydroxyalkyl, alkoxyalkyl, acyloxyalkyl, or acetyl.

10. The organometallic iron complex of claim 9, wherein $R_6$ and $R_7$ are independently selected from the group consisting of methyl and ethyl.

11. The organometallic iron complex of claim 9, wherein $R_6$ and $R_7$ are independently selected from the group consisting of piperidino

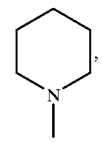

morpholino

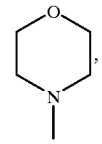

and piperazine

12. The organometallic iron complex of claim 4 having one of the following structures:

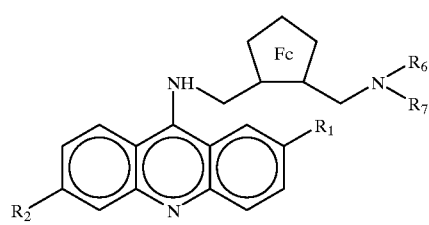

-continued

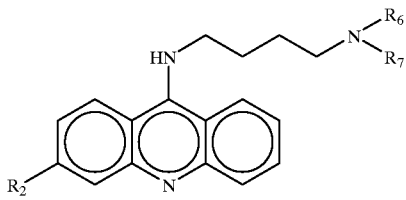

wherein $R_6$ and $R_7$ are independently selected from the group consisting of hydrogen, alkyl-ferrocenyl, ferrocenyl, alkyl, and the group

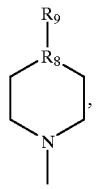

where $R_8$ is —$CH_2$— or a heteroatom, and $R_9$ is hydrogen, alkyl, alkoxy, acyl, halogen or etheralkyl aldehyde, hydroxyl, hydroxyalkyl, alkoxyalkyl, acyloxyalkyl, acetylalkyl.

13. The organometallic iron complex of claim 1 having one of the following structures:

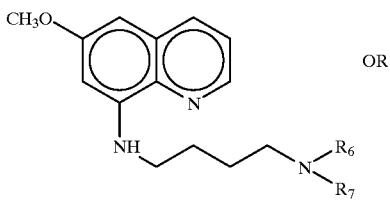

OR

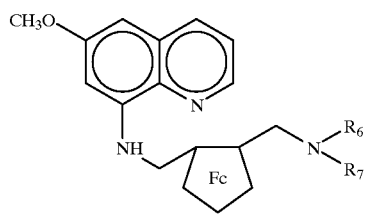

wherein $R_6$ and $R_7$ are independently selected from the group consisting of hydrogen, alkyl-ferrocenyl, ferrocenyl, alkyl, and the group

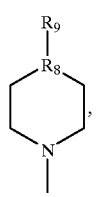

where $R_8$ is —$CH_2$— or a heteroatom, and $R_9$ is hydrogen, alkyl, alkoxy, acyl, halogen or etheralkyl aldehyde, hydroxyl, hydroxyalkyl, alkoxyalkyl, acyloxyalkyl, acetylalkyl.

14. A composition for the treatment of malaria comprising an organometallic iron complex of claim 1 in combination with an acceptable pharmaceutical excipient.

15. A method of treating malaria comprising administering to an individual with malaria an amount of an organometallic iron complex of claim 1 which is sufficient to provide effective treatment to said individual.

16. The organometallic iron complex of claim 12, wherein $R_6$ and $R_7$ are independently selected from the group consisting of piperidio

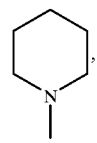

morpholino

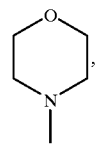

and piperazine

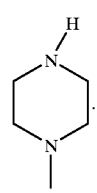

17. The organometallic iron complex of claim 13, wherein $R_6$ and $R_7$ are independently selected from the group consisting of piperidino

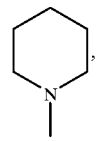

morpholino

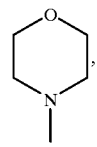

and piperazine.

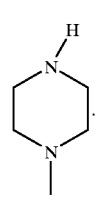

* * * * *